(12) United States Patent
Philippe et al.

(10) Patent No.: US 6,322,800 B1
(45) Date of Patent: Nov. 27, 2001

(54) EMULSION AND COMPOSITION COMPRISING A FLUOROHYDROCARBON COMPOUND AND A METHOD FOR PREPARING SUCH AN EMULSION AND COMPOSITION

(75) Inventors: Michel Philippe, Wissous; Jean-Christophe Henrion, Pantin; Luc Nicolas-Morgantini, Rully; Agnès Dardenne, Aulnay sous Bois; Eric Bollens, Saint Maurice, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/359,367

(22) Filed: Jul. 23, 1999

Related U.S. Application Data

(62) Division of application No. 08/630,843, filed on Apr. 11, 1996.

(30) Foreign Application Priority Data

Apr. 11, 1995 (FR) .................................................. 95-04336
Apr. 11, 1995 (FR) .................................................. 95-04337

(51) Int. Cl.$^7$ ................................ A61K 7/00; A61K 7/48; A61K 7/06
(52) U.S. Cl. ............................ 424/401; 424/62; 424/70.1; 514/937; 514/938; 514/759
(58) Field of Search .................................... 424/401, 70.1, 424/62; 514/937, 938, 759

(56) References Cited

U.S. PATENT DOCUMENTS

| 3,993,744 | * | 11/1976 | Cella et al. | .............................. 424/70 |
| 5,851,539 | * | 12/1998 | Mellul et al. | ........................ 424/401 |

FOREIGN PATENT DOCUMENTS

| 595683 | 5/1994 | (EP) . |
| 595 683 A1 | * 5/1994 | (EP) . |
| 609131 | 8/1994 | (EP) . |
| 609132 | 8/1994 | (EP) . |
| 609 1312 A1 | * 8/1994 | (EP) . |
| 629394 | 12/1994 | (EP) . |
| 1 598 567 | * 9/1981 | (GB) . |
| WO 93/11103 | 6/1993 | (WO) . |

\* cited by examiner

*Primary Examiner*—Thurman K. Page
*Assistant Examiner*—Lakshmi Channavajjala
(74) *Attorney, Agent, or Firm*—Finnegan, Henderson, Farabow, Garrett & Dunner, LLP

(57) ABSTRACT

A fluorohydrocarbon compound of formula $R_F$—$C_2H_4$—O—CO—$R_H$, in which $R_F$ is a perfluorinated alkyl group and $R_H$ is an alkyl group, in and/or for the preparation of a stable emulsion containing at least one fatty phase and one aqueous phase. The invention also relates to the use of the same compound as a stabilizing agent for an emulsion containing at least one fatty phase and one aqueous phase. Another subject of the invention is the use of such a compound as an essential component of the fatty phase of an emulsion and emulsions containing such a fatty phase. Another subject of the invention is a composition comprising such an emulsion.

16 Claims, No Drawings

EMULSION AND COMPOSITION COMPRISING A FLUOROHYDROCARBON COMPOUND AND A METHOD FOR PREPARING SUCH AN EMULSION AND COMPOSITION

This is a division of co-pending application Serial No. 08/630,843, filed Apr. 11, 1996, which is incorporated herein by reference.

The present invention relates to the use of a fluorohydrocarbon compound in an emulsion, in particular as a stabilizing agent or as an essential compound of the fatty phase. The invention also relates to a composition comprising the emulsion, in particular a cosmetic, hygiene or pharmaceutical composition.

The use of perfluoropolyethers is known, in particular in the field of cleansing, protecting and making up the skin or hair. These compounds are known for their low surface tension and their ease of spreading, but they have a greatly reduced solubility in the majority of fluids, except in fluorinated fluids, which makes their formulation in cosmetics very difficult. Some of these compounds, particularly perfluoro(methyl isopropyl ether)s, are known under the name of FOMBLIN HC and are marketed by Montefluo.

Fluorohydrocarbon compounds exhibiting good solubility, in particular in conventional solvents, are known, for example, from the document FR 2,684,668. They make it possible to obtain stable and homogeneous emulsions. The thermodynamic stability of the emulsions comprising these compounds, in particular when they make up the whole of the fatty phase, could especially be improved.

The Inventors were faced with the problem of further improving the quality and the stability of the emulsions, whatever the nature of the oils employed.

The aim of the present invention is to provide fluorohydrocarbon compounds for the preparation of an emulsion of improved quality and stability with respect to those known in the state of the art. The fluorohydrocarbon compounds of the invention can indeed be incorporated as a stabilizing agent for an emulsion containing at least one fatty phase and one aqueous phase. They can in addition be used as an essential constituent of the fatty phase of an emulsion.

The subject of the invention is the use of at least one compound of formula (I):

$$R_F\text{—}C_2H_4\text{—}O\text{—}CO\text{—}R_H \qquad (I)$$

in which: $R_F$ represents a linear or branched perfluorinated alkyl-group having from 4 to 20 carbon atoms, and $R_H$ represents a linear or branched alkyl group having from 1 to 29 carbon atoms, in and/or for the preparation of a stable emulsion containing at least one fatty phase and one aqueous phase.

A further subject of the invention is the use of at least one fluorohydrocarbon compound of formula (I) as a stabilizing agent in an emulsion containing at least one fatty phase and one aqueous phase.

It has in fact been observed that the presence of at least one compound of formula (I) or of a mixture of these compounds when more than one compound of formula (I) is used, in an emulsion, and in particular in the fatty phase of the emulsion, can make it possible to improve the stability of the said emulsion, whatever the chemical nature of the fatty phase employed.

For the compounds of formula (I), the $R_F$ radical can preferably represent a perfluorinated alkyl group having from 4 to 10 carbon atoms and the $R_H$ radical a linear or branched alkyl group having from 1 to 15 carbon atoms.

Mention may be made, among the compounds of formula (I) which can be used in the emulsion according to the invention, of 2-(F-octyl)ethyl hexanoate, 2'-(F-hexyl)ethyl 2-butyloctanoate, 2'-(F-hexyl)ethyl 2-ethylhexanoate, 2-(F-octyl)ethyl 2-decyltetradecanoate, 2-(F-hexyl)ethyl octanoate, 2-(F-octyl)ethyl octanoate, 2-(F-octyl)ethyl octadecanoate, 2-(F-octyl)ethyl docosanoate, and 2-(F-octyl)ethyl decanoate.

When the compound of formula (I) is used as stabilizing agent, it can be present in the emulsion, preferably in the fatty phase, in the proportion generally ranging from 0.1 to 30% by weight, and preferably ranging from 0.5–20% by weight.

The fatty phase of the emulsion can additionally comprise at least one oil that can be chosen in particular from hydrocarbon oils that are optionally fluorinated, silicone oils and perfluorinated oils, alone or as a mixture.

The compound of formula (I) can be present in the composition in an amount generally ranging from 0.01 to 60% by weight, and preferably from 0.1 to 20% by weight, with respect to the total weight of the composition.

Another subject of the invention is the use of at least one compound of formula (I) as an essential constituent of the fatty phase of an emulsion.

It has indeed been surprisingly observed that the fact that the fatty phase comprises essentially at least one compound of formula (I), or a mixture of compounds of formula (I), can make it possible to thermodynamically stabilize the emulsion with time.

Another subject of the invention is an emulsion comprising at least one fatty phase and one aqueous phase, the fatty phase being composed essentially of at least one fluorohydrocarbon compound of formula (I).

The present invention also relates to a cosmetic, hygiene or pharmaceutical, including food, composition comprising an emulsion containing at least one aqueous phase and one fatty phase composed essentially of at least one compound of formula (I). "Composed essentially of" is understood to mean in the present description that the fatty phase comprises the compound of formula (I), or a mixture of compounds of formula (I), as the sole liquid oil, the compound preferably representing at least 50% by weight of the fatty phase; the fatty phase can then comprise 0–50% of conventional lipophilic additives other than oils. The compound of formula (I), or a mixture of these compounds, preferably represents at least 75% by weight of the fatty phase.

Whatever the use of the compound of formula (I), the fatty phase of the emulsion can comprise fat-soluble additives conventionally used in the field of application, such as vitamins, fragrances, fatty acids, waxy lipids, and in particular, ceramides.

The aqueous phase of the emulsions of the invention can also comprise conventionally-used hydrophilic additives, such as glycerol and urea.

The aqueous phase/oily phase ratio in the emulsions can range from 9 to 0.1 and preferably from 5 to 1.5. The emulsion can thus be provided in the water-in-oil or oil-in-water form or indeed in the form of a multiple emulsion.

The emulsions according to the invention can be used as a composition, or in a composition, in particular in the cosmetic, hygiene and pharmaceutical or indeed food fields. The composition can be provided in particular in the form of a gel, a milk or a cream.

In particular, the composition can be provided in the form of a product intended for making up and/or for caring for the skin or keratinous substances or alternatively in the form of a product for dyeing the hair or of a product for protecting the skin and/or keratinous substances from the sun.

The compositions in accordance with the invention can comprise any additive commonly used in the field under consideration, such as surfactants, moisturizing agents, organic solvents, silicones, thickeners, emollients, sunscreens, treating agents, anti-foaming agents, fragrances, preservatives, antioxidizing agents, sequestrants, flavouring agents, basifying or acidifying agents, fillers and pigments, emulsifiers or coemulsifiers.

The compound of formula (I) can be prepared according to a conventional esterification process that comprises mixing, in acid medium, preferably in the presence of a solvent, an acid of formula $R_H$—COOH with an alcohol of formula $R_F$—$C_2H_4$—OH in which the $R_H$ and $R_F$ radicals have the same meanings as above.

Another esterification process for preparing the compound of formula (I) comprises reacting an alcohol of formula $R_F$—$C_2H_4$—OH with an activated acid derivative of formula $R_H$—CO—Y in which $R_H$ has the same meaning as above and Y represents an activating group, in particular of halogen, mixed or symmetrical anhydride residue or imidazole type.

The invention will now be described in greater detail by means of the following examples, which are given solely by way of illustration and in no way limit the invention. Examples 1 to 7 describe a process for the preparation of compounds used in the context of the present invention.

PREPARATION EXAMPLES

Example 1

Preparation of 2-(F-hexyl)ethyl 2-ethylhexanoate 114.66 g of 2-(F-hexyl) ethanol and 43.2 g of 2-ethylhexanoic acid were introduced into 850 ml of toluene in the presence of 9 g of para-toluenesulphonic acid monohydrate in a 1 litre reactor. The reaction mixture was brought to reflux of the solvent for 16 hours. The solution was concentrated to obtain an oil that was distilled to obtain 113 g of compound (77% yield).

Chemical analysis of the product obtained gave:

Boiling temperature: 105° at 0.3 mbar $^{13}$C NMR spectrum: conformed to the expected structure Mass spectrum: conformed to the expected structure Elemental analysis:

|  | % C | % H | % F |
| --- | --- | --- | --- |
| Theoretical | 39.20 | 3.91 | 50.37 |
| Calculated | 39.23 | 3.81 | 50.42 |

Example 2

Preparation of 2-(F-hexyl)ethyl octanoate 43.2 g of octanoic acid and 114.7 g of 2-(F-hexyl) ethanol were dissolved in 850 ml of toluene in the presence of 9 g of para-toluenesulphonic acid in a 2 litre reactor. The mixture was heated at reflux for 16 hours, and the solvent was then evaporated to obtain an oil that was taken up in 800 ml of ethanol. This solution was stirred for 15 minutes in the presence of 150 g of resin washed beforehand with water, with a 50/50 ethanol/water mixture and then with ethanol alone. The resin was filtered on sintered glass, and the solvent was then evaporated to obtain an oil that was distilled under vacuum to provide 110 g of the product (75% yield).

Chemical analysis of the product obtained gave:

Boiling temperature: 105° C. at 0.4 mbar

Mass spectrum: conformed to the expected structure

Elemental analysis:

|  | % C | % H | % F |
| --- | --- | --- | --- |
| Theoretical | 39.20 | 3.91 | 50.37 |
| Calculated | 39.31 | 3.97 | 50.67 |

Example 3

Preparation of 2-(F-hexyl)ethyl 2-butyloctanoate 76.44 g of 2-(F-hexyl)ethanol and 40 g of 2-butyloctanoic acid were introduced into 850 ml of toluene in the presence of 6 g of para-toluenesulphonic acid monohydrate in a 1.5 litre reactor. The reaction mixture was brought to reflux for 16 hours. The solution was concentrated to obtain an oil that was distilled to obtain the expected compound (73% yield).

Chemical analysis of the product obtained gave:

Boiling temperature: 136–140° C. at 0.6 mbar

Mass spectrum: conformed to the expected structure $^{13}$C NMR spectrum: conformed to the expected structure Elemental analysis:

|  | % C | % H | % F |
| --- | --- | --- | --- |
| Theoretical | 43.96 | 4.98 | 45.20 |
| Calculated | 43.84 | 4.91 | 45.49 |

Example 4

Preparation of 2-(F-octyl)ethyl 2-decyltetradecanoate 69.6 g of 2-(F-octyl)ethanol and 46.8 g of 2-decyltetradecanoic acid were introduced into 640 ml of toluene in the presence of 4.49 g of para-toluenesulphonic acid monohydrate in a 1 litre reactor. The reaction mixture was brought to reflux of the solvent for 16 hours. The solvent was evaporated to obtain an oil that precipitated by addition of 500 ml of ethanol. The solid obtained was filtered and washed twice with ethanol. After drying under reduced pressure, 78 g of a white solid were obtained (76% yield).

Chemical analysis of the product obtained gave:

Melting temperature: 43° C.

Mass spectrum: conformed to the expected structure $^{13}$C NMR spectrum: conformed to the expected structure Elemental analysis:

|  | % C | % H | % F |
| --- | --- | --- | --- |
| Theoretical | 50.12 | 6.31 | 39.64 |
| Calculated | 50.06 | 6.26 | 39.64 |

Example 5

Preparation of 2-(F-octyl)ethyl octadecanoate 69.6 g of 2-(F-octyl)ethanol were dissolved in 200 ml of tetrahydrofuran in a 1 litre round-bottomed flask and then 12.64 g of pyridine were added. The solution was cooled to 5° C, and 45.38 g of stearoyl chloride in 100 ml of tetrahydrofuran were run in over 30 minutes with stirring. The reaction mixture was then allowed to return to room temperature and was allowed to stir for 1 hour.

The mixture was concentrated and the expected product was precipitated by addition of 500 ml of ethanol. The solid obtained was filtered, washed, and recrystallized from ethanol. After drying under reduced pressure, 58 g of a white solid were obtained (53% yield).

Analysis of the product obtained gave:

Melting temperature: 40° C.

Mass spectrum: conformed to the expected structure

Elemental analysis:

|  | % C | % H | % F |
|---|---|---|---|
| Theoretical | 46.03 | 5.38 | 44.21 |
| Calculated | 46.44 | 5.42 | 43.53 |

Example 6

Preparation of 2-(F-octyl)ethyl hexanoate 34.8 g of hexanoic acid and 146.16 g of 2-(F-octyl) ethanol were dissolved in 850 ml of toluene in the presence of 9 g of para-toluenesulphonic acid in a 2 litre reactor. The mixture was heated at reflux for 36 hours, and the solvent was then evaporated to obtain an oil that was taken up in 600 ml of ethanol. This solution was stirred for 15 minutes in the presence of 150 g of resin washed beforehand with water, a 50/50 ethanol/water mixture, and then ethanol alone. The resin was filtered on sintered glass, and the solvent was then evaporated to obtain an oil that was distilled under reduced pressure to provide 143 g (0.254 mol) of the expected ester (85% yield).

Chemical analysis of the product obtained gave:

Boiling temperature: 107–112° C. at 0.4 mbar

Mass spectrum: conformed to the expected structure $^1$H and $^{13}$C NMR spectrum: conformed to the expected structure Elemental analysis:

|  | % C | % H | % F |
|---|---|---|---|
| Theoretical | 34.18 | 2.69 | 57.44 |
| Calculated | 34.12 | 2.73 | 54.59 |

Example 7

Preparation of 2-(F-octyl)ethyl docosanoate 97.44 g of 2-(F-octyl)ethanol and 68 g of docosanoic acid were introduced into 800 ml of toluene in the presence of 6 g of para-toluenesulphonic acid monohydrate in a 1 litre reactor. The reaction mixture was brought to reflux of the solvent for 24 hours. The solvent was evaporated to obtain a wax that was recrystallized from absolute ethanol. 132.2 g of a white solid (84% yield) were finally obtained.

Chemical analysis of the product obtained gave:

Melting temperature: 70.6° C.

Mass spectrum: conformed to the expected structure $^{13}$C NMR spectrum: conformed to the expected structure Elemental analysis:

|  | % C | % H | % F |
|---|---|---|---|
| Theoretical | 48.86 | 6.02 | 41.05 |
| Calculated | 49.02 | 6.01 | 40.81 |

EXAMPLES IN WHICH AN EMULSION ACCORDING TO THE INVENTION CONTAINING A COMPOUND OF FORMULA (I) AS A STABILIZING AGENT IS COMPARED WITH AN EMULSION OF THE PRIOR ART

Example 8: Comparative Example

This example compares the stability of a stabilized emulsion according to the invention with a stabilized emulsion according to the prior art (FR 2,684,668).

Invention (% by weight):

| | |
|---|---|
| Compound of Example 1 | 4.5% |
| silicone oil (cyclopentadimethylsiloxane) | 45.5% |
| emulsifier (80% methacrylic acid/20% lauryl methacrylate polymer, 80% neutralized) | 1% |
| water | q.s. for 100% |

Prior art (% by weight):

| | |
|---|---|
| 1-(2'-(F-hexyl)ethylthio)-3-(2"-ethylhexyloxy)-2-propanol | 4.5% |
| silicone oil (cyclopentadimethylsiloxane) | 45.5% |
| emulsifier (polymer consisting of 80% of methacrylic acid and 20% of lauryl methacrylate, 80% neutralized) | 1% |
| water | q.s. for 100% |

The stability of the emulsion according to the invention was markedly greater compared to that of the emulsion of the state of the art. In fact, the emulsion according to the invention remained stable for more than 100 days, during storage at 20° C., whereas the emulsion according to the state of the art remained stable for only approximately 35 days; demixing of the emulsion was then observed.

Example 9: Comparative Example

The stability of emulsions comprising the stabilizing agent according to the invention was compared with the same emulsions without the stabilizer.

The following results were obtained:

1st comparison

Invention (% by weight):

| | |
|---|---|
| Compound of Example 1 | 10% |
| triglycerides of caprylic and capric acids | 40% |
| emulsifier (80% methacrylic acid/20% lauryl methacrylate polymer, 80% neutralized) | 1% |
| water | q.s. for 100% |

Prior Art

| | |
|---|---|
| triglycerides of caprylic and capric acids | 50% |
| emulsifier (80% methacrylic acid/20% lauryl methacrylate polymer, 80% neutralized) | 1% |
| water | q.s. for 100% |

The stability of the emulsion according to the invention was markedly greater compared to that of the emulsion of the state of the art. The emulsion according to the invention remained stable for more than 80 days, during storage at 20° C., whereas the emulsion according to the state of the art remained stable for only approximately 9 days under the same conditions.

2nd comparison

Invention (% by weight):

| | |
|---|---|
| Compound of example 2 | 10% |
| palmitic ester of 2-ethylhexyl glyceryl ether | 40% |
| emulsifier (80% methacrylic acid/20% lauryl methacrylate polymer, 80% neutralized) | 1% |
| water | q.s. for 100% |

Prior Art

| | |
|---|---|
| palmitic ester of 2-ethylhexyl glyceryl ether | 50% |
| emulsifier (80% methacrylic acid/20% lauryl methacrylate polymer, 80% neutralized) | 1% |
| water | q.s. for 100% |

The stability of the emulsion according to the invention was markedly greater compared to that of the emulsion of the state of the art. The emulsion according to the invention remained stable for more than 80 days, during storage at 20° C., whereas the emulsion according to the state of the art remained stable for only approximately 45 days under the same conditions.

3rd comparison

Invention (% by weight):

| | |
|---|---|
| Compound of Example I | 10% |
| cyclopentadimethylsiloxane | 40% |
| emulsifier (80% methacrylic acid/20% lauryl methacrylate polymer, 80% neutralized) | 1% |
| water | q.s. for 100% |

Prior Art

| | |
|---|---|
| cyclopentadimethylsiloxane | 50% |
| emulsifier (80% methacrylic acid/20% lauryl methacrylate polymer, 80% neutralized) | 1% |
| water | q.s. for 100% |

The stability of the emulsion according to the invention was markedly greater compared to that of the emulsion of the state of the art. The emulsion according to the invention remained stable for more than 15 days, during storage at 20° C., whereas the emulsion according to the state of the art remained stable for only approximately 7 days under the same conditions.

EMULSION EXAMPLES IN WHICH THE FATTY PHASE IS COMPOSED ESSENTIALLY OF A COMPOUND OF FORMS (I)

Example A: Emulsion Example

An emulsion was prepared comprising (% by weight):

| | |
|---|---|
| Compound of Example I | 50% |
| emulsifier (polymer consisting of 80% of methacrylic acid and 20% of lauryl methacrylate, 80% neutralized) | 1% |
| water | q.s. for 100% |

The emulsion obtained was provided in a viscous, opaque, homogeneous and opalescent form. The size of the globules was approximately 0.5 μm.

Example B: Emulsion Example

An emulsion was prepared comprising (% by weight):

| | |
|---|---|
| Compound of Example 2 | 50% |
| emulsifier (polymer consisting of 80% of methacrylic acid and 20% of lauryl methacrylate, 80% neutralized) | 1% |
| water | q.s. for 100% |

The emulsion obtained was in a viscous, opaque, homogeneous and opalescent form. The size of the globules was approximately 0.5 μm.

Example C: Comparative Example

This example compares the stability of an emulsion according to the invention (Example A) with an emulsion of the prior art (FR 2,684,668) that has the following composition (% by weight):

| | |
|---|---|
| 1-(2'-(F-Hexyl)ethylthio)-3-(2"-ethylhexyloxy)-2-propanol | 50% |
| emulsifier (polymer consisting of 80% of methacrylic acid and 20% of lauryl methacrylate, 80% neutralized) | 1% |
| water | q.s. for 100% |

The stability of the emulsion according to the invention was markedly greater compared to that of the emulsion of the state of the art. In fact, the emulsion according to the invention remained stable for more than 20 days, during storage at 20° C., whereas the emulsion according to the state of the art remained stable for only approximately 15 days; demixing of the emulsion was then observed.

We claim:

1. A method of preparing an emulsion of improved stability containing at least one fatty phase and one aqueous phase, comprising:

incorporating into the at least one fatty phase 0.1 to 30% by weight of at least one fluorohydrocarbon compound of formula (I):

$$R_F\text{—}C_2H_4\text{—}O\text{—}CO\text{—}R_H \qquad (I)$$

wherein $R_F$ represents a linear or branched perfluorinated alkyl group having from 4 to 20 carbon atoms, and $R_H$ represents a linear or branched alkyl group having from 1 to 29 carbon atoms.

2. A method according to claim 1, wherein $R_F$ is a perfluorinated alkyl group having from 4 to 10 carbon atoms.

3. A method according to claim 1, wherein $R_H$ is a linear or branched alkyl group having 1 to 15 carbon atoms.

4. A method according to claim 1, wherein the compound of formula (I) is 2(F-octyl)ethyl hexanoate, 2'-(F-hexyl)ethyl 2-butyloctanoate, 2'-(F-hexyl)ethyl 2ethylhexanoate, 2'-(F-octyl)ethyl 2-decyltetradecanoate, 2-(F-hexyl)ethyl octanoate, 2-(F-octyl)ethyl octanoate, 2-(F-octyl)ethyl octadecanoate, 2-(F-octyl)ethyl docosanoate or 2-(F-octyl) ethyl decanoate.

5. A method of improving the stability of an emulsion containing at least one fatty phase and one aqueous phase comprising the step of including in the at least one fatty phase 0.1 to 30% by weight of at least one fluorohydrocarbon compound of formula (1) as defined in claim 1.

6. A method according to claim 5, wherein the compound of formula (I) is present in the emulsion in an amount ranging from 0.5 to 20% by weight.

7. A method according to claim 5, wherein the fatty phase of the emulsion comprises at least one oil.

8. A method according to claim 7, wherein said at least one oil is hydrocarbon oil, silicone oil, or perfluorinated oil.

9. A method according to claim 8, wherein said hydrocarbon oil is fluorinated.

10. A method according to claim 5, wherein the emulsion is an oil-in-water or water-in-oil emulsion or a multiple emulsion.

11. A method according to claim 5, wherein the aqueous phase/oily phase ratio ranges from 9:1 to 0.1:1.

12. A method according to claim 11, wherein the aqueous phase/oily phase ratio ranges from 5:1 to 1.5:1.

13. A method of preparing a cosmetic, hygiene, pharmaceutical, or food product comprising:

forming at least one emulsion of improved stability containing at least one fatty phase and one aqueous phase, incorporating into the at least one fatty phase 0.1 to 30% by weight of at least one fluorohydrocarbon compound of formula (I):

$$R_F\text{—}C_2H_4\text{—}O\text{—}CO\text{—}R_H \qquad (I)$$

wherein $R_F$ represents a linear or branched perfluorinated alkyl group having from 4 to 20 carbon atoms, and $R_H$ represents a linear or branched alkyl group having from 1 to 29 carbon atoms; and incorporating the at least one emulsion into the product.

14. A method of preparing a product for making up or for caring for the skin or keratinous substances or a product for dyeing the hair or a product for protecting the skin or keratinous substances from the sun comprising:

forming at least one emulsion of improved stability containing at least one fatty phase and one aqueous phase, incorporating into the at least one fatty phase 0.1 to 30% by weight of at least one fluorohydrocarbon compound of formula (I):

$$R_F\text{—}C_2H_4\text{—}O\text{—}CO\text{—}R_H \qquad (I)$$

wherein $R_F$ represents a linear or branched perfluorinated alkyl group having from 4 to 20 carbon atoms, and $R_H$ represents a linear or branched alkyl group having from 1 to 29 carbon atoms; and incorporating the at least one emulsion into the product.

15. A method of preparing the fatty phase of an emulsion containing at least one fatty phase and one aqueous phase comprising adding as an essential constituent of said fatty phase at least one fluorohydrocarbon compound of formula (I):

$$R_F\text{—}C_2H_4\text{—}O\text{—}CO\text{—}R_H \qquad (I)$$

wherein $R_F$ represents a linear or branched perfluorinated alkyl group having from 4 to 20 carbon atoms, and $R_H$ represents a linear or branched alkyl group having from 1 to 29 carbon atoms.

16. A method according to claim 1, wherein the compound of formula (I) is present in the emulsion in an amount ranging from 0.5 to 20% by weight.

* * * * *

UNITED STATES PATENT AND TRADEMARK OFFICE
CERTIFICATE OF CORRECTION

PATENT NO. : 6,322,800 B1
DATED : November 27, 2001
INVENTOR(S) : Michel Philippe et al.

It is certified that error appears in the above-identified patent and that said Letters Patent is hereby corrected as shown below:

Column 9, claim 4,
Line 7, "2(F-octyl)ethyl" should read -- 2-(F-octyl)ethyl --.
Line 8, "2ethylhexanoate" should read -- 2-ethylhexanoate --.
Line 11, "docosanoate or" should read -- docosanoate, or --.

Column 9, claim 5,
Line 16, "(l)" should read -- (I) --.

Signed and Sealed this

Ninth Day of April, 2002

Attest:

Attesting Officer

JAMES E. ROGAN
Director of the United States Patent and Trademark Office